United States Patent [19]

Ueda et al.

[11] Patent Number: 4,749,574

[45] Date of Patent: Jun. 7, 1988

[54] SUSTAINED-RELEASE TRANSDERMAL DELIVERY PREPARATIONS

[75] Inventors: Yoshio Ueda, Mikagenaka; Sotoo Asakura, Ooeni; Yoshio Murakami, Takatsuki; Fumio Shimojo, Kawani; Kazutake Kado, Ikeda, all of Japan

[73] Assignee: Fujisawa Pharmaceutical Co., Ltd., Osaka, Japan

[21] Appl. No.: 32,628

[22] Filed: Apr. 1, 1987

[30] Foreign Application Priority Data

Apr. 14, 1986 [JP] Japan ................................. 61-86589

[51] Int. Cl.$^4$ ............................................. A61F 13/03
[52] U.S. Cl. ..................................... 424/448; 424/449
[58] Field of Search ............................... 424/448, 449

[56] References Cited

U.S. PATENT DOCUMENTS 3,742,951 7/1973 Zaffaroni .

FOREIGN PATENT DOCUMENTS 0193164 9/1986 European Pat. Off. .

OTHER PUBLICATIONS

Patent Abstracts of Japan, vol. 9, No. 324 (C-320) [2047], 12/17/85 & JPA-60 156 607.
Chemical Abstracts, vol. 100, No. 20, May 14, 1984, p. 327, Abstract No. 161803n.

*Primary Examiner*—Thurman K. Page
*Assistant Examiner*—L. R. Horne
*Attorney, Agent, or Firm*—Oblon, Fisher, Spivak, McClelland & Maier

[57] ABSTRACT

The invention relates to a sustained-release transdermal delivery preparation which comprises a slow-release microcapsule containing 2-nitroxymethyl-6-chloropyridine or its occlusion compound with $\beta$-cyclodextrin and a skin-compatible base.

5 Claims, No Drawings

SUSTAINED-RELEASE TRANSDERMAL DELIVERY PREPARATIONS

The present invention relates to a sustained-release transdermal delivery preparation containing 2-nitroxymethyl-6-chloropyridine, which is represented by the following chemical formula;

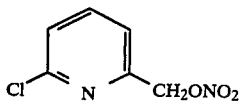

or its occlusion compound with β-cyclodextrin.

More particularly, the present invention relates to a transdermal delivery preparation rendered long-acting by such means of controlling the rate of release of the active ingredient 2-nitroxymethyl-6-chloropyridine as microencapsulation, interposition of a membrane, dispersion in a polymer matrix and/or dispersion in a suitable gel for the purpose of controlling the blood concentration of said active ingredient at a constant level for an extended time and assuring a sustained efficacy.

2-Nitroxymethyl-6-chloropyridine which is employed in accordance with the invention has vasodilating activity and is of value as a therapeutic agent for vascular disorder.

Generally, with regard to nitrate compounds, which are represented by nitroglycerin and also include 2-nitroxymethyl-6-chloropyridine, it is well known that after their oral administration, the rate of their absorption into blood and disappearance therefrom are very fast, and the therefore such compounds have the disadvantage of the short effective time.

After an intensive study, the present inventors found that 2-nitroxymethyl-6-chloropyridine is excellent in percutaneous absorption and by the various alternative methods to be described hereinafter, ultimately succeeded in preparing a transdermal delivery preparation adapted to release the active drug at a controlled rate over a protracted period of time. The present invention accordingly accomplished has overcome the above-mentioned problems by providing a long-sustained efficacy.

As a method for controlling the percutaneous absorption rate of the active ingredient in the sustained-release transdermal delivery preparation of the present invention, there may be mentioned the method in which the active compound is first formulated into slow-release microcapsules which are then dispersed in a dermatological or skin-compatible base.

Such slow-release microcapsules can be prepared in a conventional manner. For examples, the slow-release microcapsule is prepared by coating a granule containing the drug with a basic lubricant membrane, which can control the release rate of the drug.

The granules containing the drug is prepared by mixing the drug, excipient (e.g. cane sugar, lactose, sucrose, mannite, etc.) and other additives commonly used in this field in a conventional manner.

The amount of the drug is preferably 10 to 70 weight percent of the whole granule components, more preferably 40 to 60 weight percent of the whole granule components, but the amount of the drug is not restricted to the above range and may be determined fittingly depending on the intended duration of the drug release, or the like.

In these procedures, 2-nitroxymethyl-6-chloropyridine, the active principal, is such an oily and volatile substance that, this granule may be preferably prepared after conversion of 2-nitroxymethyl-6-chloropyridine to its occlusion compound with β-cyclodextrin.

Such bed granules are coated with a basic lubricant membrane which can control the release rate of the drug.

The basic lubricant membrane used here should be independent of pH of an outer medium, and may include a coating material such as acrylate resin [e.g. dimethylaminoethylmethacrylate - methylmetacrylic acid copolymer (e.g. Eudragit E 30 D etc.)], shellac, cellulose derivatives [e.g. ethylcellulose, hydroxypropyl-methylcellulose, etc.], or the like.

The amount of the coating material is preferably 0.1 to 20 weight percent of the whole bed granule containing the drug, but the amount is not restricted to the above range and should be selected depending on the intended duration of drug release, or the like.

The coating treatment may be carried out with a fluid bed granulator in a conventional manner.

However, this is not an exclusive choice but any other known microencapsulation method such as coacervation, interfacial polymerization, spray-drying, etc. can be utilized.

These slow-release microcapsules are then dispersed in a skin-compatible base. As this skin-compatible base, any dermatologically acceptable base can be employed only if it is not contraindicated with respect to the active compound and the microcapsule wall member and not too slow in the rate of diffusion of the active compound therethrough. As examples of such base, there may be mentioned cold-or heat-curable silicone polymers (for example, silicone elastomer), hydrogels comprised of water-soluble high polymers [for example, agar, gelatin, carrageenin, chitosan, agarose, konjak, polyvinyl alcohol, polyvinylpyrrolidone, poly (2-hydroxyethyl) methacrylate, hydroxypropylmethylcellulose, carboxymethylcellulose, hydroxypropylcellulose, hydroxyethylcellulose, etc.], and products of gelatin of liquid paraffin, triglycerides, etc. with lecithin, ethylcellulose or the like. However, these bases are not exhaustive but any other suitable bases can be selected according to the intended release time and other requirements.

As an auxiliary agent for assisting in the release of the active compound, a hydrophilic solvent or a hydrophobic solvent can be incorporated in the base. Examples of such hydrophilic solvents include polyols such as propylene glycol, polyethylene glycol (e.g. PEG-400), glycerol, etc. as well as various mixtures thereof. Examples of said hydrophobic solvents include middle chain fatty acid glycerides such as panasate, miglyol, etc., liquid paraffin and so on, as well as various mixtures thereof.

Another exemplary method of controlling the percutaneous absorption rate of the active compound comprises dispersing the active compound in a suitable skin-compatible sustained-release matrix base so that the diffusion of the active compound in the base will be rate-determining. As examples of such skin-compatible bases, the bases named hereinbefore can be mentioned. If necessary, the rate of release of the drug from the base can be controlled as desired by adding said hydrophilic or hydrophobic solvent to such base.

The percutaneous absorption rate of the active compound may also be controlled by interposing a membrane of a suitable material and thickness which gives a slower diffusion rate of the active compound than the base. The release-control membrane just mentioned is preferably a film of ethylene-vinyl acetate copolymer, high density polyethylene or low density polyethylene, although these are not exclusive choices.

The proportion of 2-nitroxymethyl-6-chloropyridine in the base is 1 to 40 weight percent and preferably 2 to 20 weight percent.

Further, the preparation of the present invention can be prepared in the same manner as the conventional tape preparation. Thus, one may mix 2-nitroxymethyl-6-chloropyridine or its occlusion compound with β-cyclodextrin with a suitable adhesive agent and coat a suitable tape with the mixture. The adhesive mentioned just above may be any adhesive that can be used in the manufacture of medical tape products, and can be selected according to the desired rate of release of the active compound from among such adhesives as silicone adhesives (e.g. Medical Adhesive 355, Dow Corning Corp.), rubber type adhesives (e.g. JSR 0585, Japan Synthetic Rubber Co.), acrylic adhesives (e.g. Primal N580S, Japan Acrylic Chemical Co.) and so on.

The amount of 2-nitroxymethyl-6-chloropyridine in the adhesive base is 0.2 to 30 weight percent and preferably 1 to 15 weight percent.

It is also possible to formulate the active compound in the form of the usual ointment or cream for percutaneous absorption. Then, in order to assure a sustained release and controlled absorption of the active compound and prevent spoilage of the clothes, one may fill the preparation in a suitable container and apply it against the skin or coat the preparation in a uniform thickness on a support material such as a tape and apply the tape to the skin.

The sustained-release transdermal delivery preparation according to the present invention can also be provided in other optional forms only if they assure a sustained absorption of the active compound from the skin.

The detail of the present invention is described below using actual examples of producing preparation and evaluating their quality.

PREPARATION 1

Fuming nitric acid (1.57 ml) was added dropwise to acetic anhydride (3.54 ml) with stirring at 0° to 5° C. 2-Hydroxymethyl-6-chloropyridine (3.59 g) was added thereto. The resulting mixture was stirred for 20 minutes at 0° C. to 5° C. The resulting mixture was alkalized weakly with an aqueous potassium carbonate solution, extracted with chloroform, washed with water, dried over anhydrous magnesium sulfate, and concentrated under reduced pressure. The residue obtained was subjected to column chromatography on aluminum oxide (40 g) and eluted with toluene. The fractions containing the desired compound were concentrated under reduced pressure to give colorless viscous oil of 2-nitroxymethyl-6-chloropyridine (2.9 g).

IR (Nujol): 1636, 1585, 1563, 1439, 1281, 1160, 1138, 985, 846, 785 cm$^{-1}$.

NMR (CCl$_4$, δ): 5.47 (2H, s), 7.15–7.45 (2H, m), 7.69 (1H, dd, J=8.5 Hz, J=6 Hz).

Analysis for C$_6$H$_5$ClN$_2$O$_3$. calcd C 38.22, H 2.67, N 14.86. found C 37.97, H 2.75, N 14.95.

PREPARATION 2

In each of five centrifuge tubes, 600 mg of β-cyclodextrin was dissolved in 20 ml of distilled water. Following addition of 50, 100, 200, 300, and 400 mg of 2-nitroxymethyl-6-chloropyridine to the five centrifuge tubes, respectively, the mixtures were shaked, centrifuged and allowed to stand overnight at room temperature so as to complete crystallization.

The crystals were collected by filtration, washed with water and air-dried to give an occlusion compound of 2-nitroxymethyl-6-chloropyridine with β-cyclodextrin.

The conditions of preparing the occlusion compound of 2-nitroxymethyl-6-chloropyridine with β-cyclodextrin and the molar ratios found in the products are shown in Table 1.

The occlusion compound obtained has the following physical properties.

(i) In its X ray powder diffraction pattern, it shows peaks at about 11.5°, about 17.2° and about 18.4° which are characteristics of an occlusion compound of 2-nitroxymethyl-6-chloropyridine with β-cyclodextrin.

(ii) In its infrared absorption spectrum (Nujol), it shows absorptions at 3300, 1645, 1586, 1568, 1459, 1376, 1330, 1281, 1158, 1080, 1022, 1000, 940 and 842 cm$^{-1}$;

(iii) Sparingly soluble in water.

TABLE 1

| Conditions of preparing an occlusion compound and molar ratios | | | |
|---|---|---|---|
| Composition of mixture solution (in 20 ml of distilled water) | | | β-Cyclodextrin/ 2-nitroxymethyl-6-chloropyridine molar ratio in occlusion compound as obtained |
| Quantity of β-cyclodextrin added (mg) | Quantity of 2-nitroxymethyl-6-chloropyridine (mg) | Content of 2-nitroxymethyl-6-chloropyridine in occlusion compound as obtained (%) | |
| 600 | 50 | 15.3 | 1/1.1 |
|  | 100 | 14.5 | 1/1.0 |
|  | 200 | 16.8 | 1/1.2 |
|  | 300 | 34.2 | 1/3.1 |
|  | 400 | 34.2 | 1/3.1 |

PREPARATION 3

Preparation of Granule (1) To non-pareil (Trademark: prepared by Freund Industrial Company, 32–24 mesh) (1.0 kg) was added the occlusion compound of 2-nitroxymethyl-6-chloropyridine with β-cyclodextrin (molar ratio 1:1) (1.3 kg) which was already pulverized by jetmizer after the occlusion process.

The mixture was, then, powder-coated using 50% sucrose solution (715 g) as a binder with a fluid bed granulator (CF 360) to form bed granules (2630 g, yield 98.9%).

(2) To Non-pareil (Trademark: prepared by Freund Industrial Company, 32–24 mesh) (800 g) was added the occlusion compound of 2-nitroxymethyl-6-chloropyridine with β-cyclodextrin (molar ratio 1:1) (914 g) which was already pulverized by jetmizer after the occlusion process.

The mixture was, then, powder-coated using ethylcellulose solution (114 g of ethylcellulose 10 cps in 960 g of ethanol) as a binder with a fluid bed granulator (CF 360) to form bed granules (1736 g, yield 95%).

PREPARATION 4

Formulas of Coating Composition

Using various coating bases, the following coating compositions were prepared in a conventional manner.

|     | Eudragit E30D formulation | | |
| --- | --- | --- | --- |
| (1) | Eudragit E30D | 32.3 g | (solids 9.7 g) |
|     | Talc | 2.4 g | |
|     | PEG-6000 | 0.7 g | |
|     | Distilled water | 62.0 g | |
|     | total | 97.4 g | (solids 12.8 g) |
| (2) | Eudragit E30D | 89.0 g | (solids 26.7 g) |
|     | Talc | 6.6 g | |
|     | PEG-6000 | 1.8 g | |
|     | Distilled water | 171.0 g | |
|     | total | 268.4 g | (solids 35.1 g) |
|     | Ethylcellulose formulation | | |
| (3) | Ethylcellulose (10 pcs) | 3 g | |
|     | Ethanol | 240 g | |
|     | total | 243 g | |

PREPARATION 5

(1) By means of a fluid bed granulator (Flow Coater Mini), the bed granules (200 g) prepared in Preparation 3-(1) were coated with the coating composition prepared in Prepartion 4-(1) in a conventional manner to give microcapsules with the following coating coverage.

Coating coverage **: 6% (total weight after drying: 212.8 g) (Eudragit E30D formulation)-(Microcapsule-I).

(2) By means of a fluid bed granulator (Flow Coater Mini), the bed granules (200 g) prepared in Preparation 3-(1) were coated with the coating composition prepared in Preparation 4-(2) in a conventional manner to give microcapsules with the following coating coverage.

Coating coverage ** : 15% (total weight after drying : 235.3 g) (Eudragit E30D formulation)-(Microcapsule-II).

(3) By means of a fluid bed granulator (Flow Coater Mini), the bed granules (200 g) prepared in Preparation 3-(2) were coated with the coating composition prepared in Preparation 4-(3) in a conventional manner to give microcapsules with the following coating coverage.

Coating coverage **: 0.7% (ethylcellulose formulation)-(Microcapsule-III).

[**The coating coverage means the percentage (theoretical) of the coating composition relative to the bed granules as calculated on the assumption that 100% of the coating composition was adsorbed to the bed granules.]

EXAMPLE 1

Agar powder (40 mg) was added to a stirred mixture of water (700 ml) and glycerol (300 mg) under heating and dissolved at about 90° to 95° C. until the agar was completely dissolved. This solution was cooled to about 80° C. and degassed under reduced pressure with heating. After degassing, the same amount of water as the amount lost by evaporation was added together with Microcapsule-I prepared in Preparation 5-(1) (77 mg; 5 mg as 2-nitroxymethyl-6-chloropyridine). The mixture was stirred to give a homogenous dispersion.

The above microcapsule dispersion was cast into a 0.2 cm-deep mold with a diameter of 2.5 cm and allowed to stand at room temperature to give a sustained-release transdermal delivery preparation in the form of a pad.

EXAMPLE 2

Using Microcapsule-II prepared in Preparation 5-(2) (87 mg; 5 mg as 2-nitroxymethyl-6-chloropyridine), a sustained-release transdermal delivery preparation in the form of a pad was manufactured in the same manner as Example 1.

EXAMPLE 3

Silicone elastomer (Silastic ®, 382 medical grade elastomer, Dow Corning Corp.) (619 mg), propylene glycol (Showa Denko K.K.) (77 mg), PEG-400 (Sanyo Chemical Industries, Ltd.) (77 mg) and a cross-linking agent (Catalist M ®, Dow Corning Corp.) (3 mg) were mixed together to give a homogeneous paste. To this paste was added Microcapsule-I prepared in Preparation 5-(1) (77 mg) and the mixture was degassed under reduced pressure with stirring.

The above microcapsule dispersion was cast in a 0.2 cm-deep mold with a diameter of 2.5 cm to give a sustained-release transdermal delivery preparation in the form of a pad.

EXAMPLE 4

Microcapsule-III prepared in Preparation 5-(3) (37 g) was mixed with silicone elastomer (Silastic ®, 382 medical grade elastomer, Dow Corning Corp.) (59.4 g) and propylene glycol (3.16 g) and after the mixture was degassed under reduced pressure, a crosslinking agent (Catalyst M ®, Dow Corning Corp.) (0.42 g) was added and mixed. This mixture was coated in a thickness of about 2 mm on an aluminum foil, allowed to stand and cure at room temperature for 2 days, and cut to size to give a sustained-release transdermal delivery preparation in the form of a pad.

EXAMPLE 5

To silicone elastomer (Silastic ®, 382 medical grade elastomer, Dow Corning Corp.) (78.9 g) were added the occlusion compound of 2-nitroxymethyl-6-chloropyridine with β-cyclodextrin (molar ratio 1:1) (175 g) and propylene glycol (1.54 g) and the mixture was stirred and degassed under reduced pressure. To this mixture was added a crosslinking agent (Catalist M ®, Dow Corning Corp.) (0.32 g) and the whole composition was coated in a thickness of 2 mm on an aluminum foil using a knife coater. The product was allowed to stand and cure at room temperature for 3 days and cut to size to give a sustained-release transdermal delivery preparation in the form of a pad.

EXAMPLE 6

A silicone adhesive agent (Medical Adhesive 355, Dow Corning Corp.) (265 g) was mixed with 2-nitroxymethyl-6-chloropyridine (1 g) and the mixture was coated in a thickness of 300 μm on a silicone-treated separator using a knife coater and dried in the air. A support (a 50 μm-thick high density polyethylene film)

was superimposed on the coated-on layer, pressed and cut to size to provide an adhesive tape.

EXAMPLE 7

2-Nitroxymethyl-6-chloropyridine (2.4 g) was mixed with an acrylic adhesive base (Primal N-580S, Japan Acrylic Chemical Co.) (600 g) and the mixture was coated in a thickness of 300 μm on a release paper to give an adhesive tape with a coating thickness of 50 μm and a drug content of 100 μg/cm².

EXAMPLE 8

Plastibase 50 w (Japan Squibb Co., Ltd.) (97.5 g) was kneaded with 2-nitroxymethyl-6-chloropyridine (2.5 g) to prepare a base. Then, a laminated aluminum foil, 6×9 cm, was cupped to a size of 2.5 cm wide×4.0 cm long×0.1 cm deep and about 760 mg of the above base is filled. A low density polyethylene film (45 μm thick) was placed over it and heat-sealed. Thereafter about 40 mg of the above base was coated on top of the film to give a skin-compatible adhesive layer. The above procedure yielded a membrane-controlled release patch preparation.

EXAMPLE 9

In the same manner as Example 8 except that a medium density polyethylene film (45 μm) was heat-sealed, a membrane-controlled release patch preparation was prepared

EXAMPLE 10

In the same manner as Example 8 except that an ethylene-vinyl acetate copolymer (EVA 660, 40 μm thick) was heat-sealed, a membrane-controlled release patch preparation was provided.

EXAMPLE 11

Gelatin (6.4 g) was added to distilled water (19.1 ml) and heated at 90° C. 1 to dissolve. Then, N-HCl (6.4 g) was added thereto to acidify the solution. To this solution was added the occlusion compound of 2-nitroxymethyl-6-chloropyridine with β-cyclodextrin (molar ratio 1:1) (25.5 g) and the mixture was coated in a uniform thickness (1.5 mm) on a Teflon sheet. The product was allowed to stand and cure for 1 day in a refrigerator and cut to size to give a sustained-release transdermal delivery preparation in the form of a pad.

EXAMPLE 12

To liquid paraffin (Keydol-Witco Chemical) (405 mg) were added propylene glycol (Showa Denko K.K.) (45 mg) and Rheopal (Gelkaza: Kaihatsu Kagaku K.K.) (50 mg) and the mixture was heated at 90° C. to dissolve. To this mixture was added the occlusion compound of 2-nitroxymethyl-6-chloropyridine with β-cyclodextrin (molar ratio 1:1) (200 mg) and the whole mixture was spread on a nonwoven fabric (2.3 cm long by 2.3 cm wide) and cooled to cure to give a sustained-release transdermal delivery preparation in the form of a pad.

EXAMPLE 13

To capric acid triglyceride (Panasate 810) (6.5 g) were added propylene glycol (0.25 g) and PEG-400 (0.25 g), followed by addition of ethylcellulose (10 CPS) (3 g), and the mixture was heated at 120° C. to dissolve. The solution was cooled to 60° C. and, then the occlusion compound of 2-nitroxymethyl-6-chloropyridine with β-cyclodextrin (molar ratio 1:1) (5 g) was added and mixed. The mixture was coated on a Teflon sheet using a knife coater and cooled to give a sustained-release transdermal delivery preparation in the form of a pad.

In accordance with the present invention, 2-nitroxymethyl-6-chloropyridine or its occlusion compound with β-cyclodextrin is microencapsulated, dispersed in a slow-release matrix base or subjected to release-control membrane formation treatment, for instance, to give a sustained-release transdermal delivery preparation adapted to maintain the blood concentration of the active ingredient and, hence, the efficacy of the active ingredient over a protracted time period.

The following representative test results illustrate the effects of the sustained release transdermal delivery preparation according to the present invention.

Test Preparations

A: Preparation according to Example 1
B: Preparation according to Example 2
C: Preparation according to Example 3
D: Preparation according to Example 4
E: Preparation according to Example 11
F: Preparation according to Example 12

(I) In Vitro Dissolution Test

(a) Test method A

An in vitro ointment dissolution test apparatus designed so that the solution released at a constant temperature would flow in a constant direction on the preparation was used. As the eluent, distilled water at 35° C. was passed at a flow rate of 0.6 ml/minute. The assay was performed by the UV method (268 nm).

(b) Test method B

The isolated rat abdominal skin is placed between the sample and the released solution in the above in vitro dissolution test apparatus and the rate of release of the drug through the skin is determined. As the eluent, a 30% aqueous solution of ethanol at 35° C. is used.

(II) Blood Concentration Test

Test method C

The hair of the abdominal region of the rat (SD strain, 7 weeks old, male) was removed with an electric clipper and a depilatory cream. After 16 hours, the test preparation was placed on the abdominal region, convered with an aluminum foil precut to size which is then secured in position with an adhesive tape. Blood sampling was performed at intervals. The plasma concentration of 2-nitroxymethyl-6-chloropyridine was measured by extracting each plasma sample with n-hexane and analyzing the extract by ECD-gas chromatography.

Test method D

The hair in the thoracic region of a beagle dog weighing 10 kg was removed with an electric clipper and a depilatory cream. After 48 hours, the test preparation was placed against the unhaired skin area and secured in position with an adhesive tape. Then, a dog jacket was put on the dog for protection so that the test preparation would not be removed during the test. Blood sampling was performed at intervals. The plasma concentration of 2-nitroxymethyl-6-chloropyridine was measured by extracting each plasma sample with n-hexane and analyzing the extract by ECD-gas chromatography.

Results

The results of tests with various test preparations are shown below.

Results of the in vitro dissolution test by Test Method A

TABLE 2

| Test prepa- ration | Time course of percentage release (%) Time (in hours) | | | | | | |
|---|---|---|---|---|---|---|---|
| | 1 | 2 | 4 | 6 | 8 | 10 | 12 |
| A | 2.25 | 4.81 | 10.44 | 16.31 | 21.25 | 26.03 | 30.31 |
| B | 1.14 | 2.47 | 5.80 | 8.90 | 11.64 | 14.42 | 16.82 |
| C | 1.88 | 3.79 | 8.19 | 14.19 | 19.92 | 26.05 | 30.08 |

Results of the in vitro test by Test Method B

TABLE 3

| Test prepa- ration | Time course of percentage release ($\mu g/cm^2/hr$) Time (in hours) | | | | | | |
|---|---|---|---|---|---|---|---|
| | 1 | 3 | 5 | 7 | 15 | 23 | 25 |
| C | 25.9 | 66.6 | 70.9 | 75.0 | 61.2 | 50.4 | 38.8 |
| E | 57.4 | 120.8 | 149 | 149.6 | 90.6 | 64.0 | 68.6 |
| F | 48 | 73.8 | 55.5 | 55.0 | 53.0 | 47.9 | 53.2 |

Plasma concentration in rats, Test Method C

The results of evaluation of test preparations A, B, and C (area 4.9 cm$^2$, 5 mg of 2-nitroxymethyl-6-chloropyridine per preparation) by Test Method C are shown in Table 4.

TABLE 4

| Test prepa- ration | Number of cases | Time course of mean plasma concentration (ng/ml) Time (in hours) | | | | | | | |
|---|---|---|---|---|---|---|---|---|---|
| | | 0.5 | 1 | 2 | 4 | 7 | 10 | 20 | 24 |
| A | 4 | 23 | 25 | 31 | 36 | 50 | 59 | 74 | 59 |
| B | 3 | 13 | 14 | 12 | 14 | 13 | 15 | 32 | 18 |
| C | 5 | 15 | 12 | 18 | 27 | 39 | 43 | 26 | 33 |

Plasma concentration in dogs, Test Method D

The result of evaluation of test preparation D (4 cm×5 cm=20 cm$^2$; 100 mg of 2-nitroxymethyl-6-chloropyridine per preparation) by Test Method D is shown in Table 5.

TABLE 5

| Time (in hours) | Time course of plasma concentration after application of Test Preparation D in dogs (n = 3) | | | | | | | |
|---|---|---|---|---|---|---|---|---|
| | 0.5 | 1 | 2 | 4 | 6 | 8 | 10 | 24 | 26 |
| Plasma con- centration (ng/ml) | 10 | 14 | 15 | 14 | 14 | 16 | 14 | 9 | 7 |

It is apparent from the above dissolution and blood concentration data that the application of a release rate-controlling means such as microencapsulation, dispersion in an appropriate slow-release matrix base (or adhesive base) or interposition of a release control membrane to 2-nitroxymethyl-6-chloropyridine or its occlusion compound with β-cyclodextrin permits a free control of the release of 2-nitroxymethyl-6-chloropyridine from the preparation to thereby allow 2-nitroxymethyl-6-chloropyridine to be absorbed from the skin at a controlled rate and its blood concentration maintained over a long period of time.

What we claim is:

1. A sustained-release transdermal delivery preparation which comprises a slow-release microcapsule containing 2-nitroxymethyl-6-chloropyridine or its occlusion compound with β-cyclodextrin and a skin-compatible base.

2. A sustained-release transdermal delivery preparation of claim 1, which is a dispersion of slow-release microcapsules each composed of 2-nitroxymethyl-6-chloropyridine or its occlusion compound with β-cyclodextrin and an encapsulating base in a skin-compatible base.

3. A sustained-release transdermal delivery preparation of claim 1, which comprises 2-nitroxymethyl-6-chloropyridine or its occlusion compound with β-cyclodextrin and a slow-release matrix base.

4. A sustained-release transdermal delivery preparation of claim 1, which comprises 2-nitroxymethyl-6-chloropyridine or its occlusion compound with β-cyclodextrin and an adhesive agent.

5. A sustained-release transdermal delivery preparation of claim 1, which comprises 2-nitroxymethyl-6-chloropyridine or its occlusion compound with β-cyclodextrin and a release control membrane.

* * * * *